United States Patent [19]

Schär

[11] Patent Number: 4,657,235

[45] Date of Patent: Apr. 14, 1987

[54] PATIENT'S TABLE

[75] Inventor: Hugo Schär, Flaach, Switzerland

[73] Assignee: BBC Brown, Boveri & Company, Limited, Baden, Switzerland

[21] Appl. No.: 763,282

[22] Filed: Aug. 7, 1985

[30] Foreign Application Priority Data

Aug. 14, 1984 [CH] Switzerland ............... 3904/84

[51] Int. Cl.4 .............................................. A61G 13/00
[52] U.S. Cl. ........................................ 269/322; 384/26
[58] Field of Search ............... 378/208, 209; 308/3 A; 384/492; 108/143; 269/322-328

[56] References Cited

U.S. PATENT DOCUMENTS 3,843,112 10/1974 McDonald ................ 269/322
3,897,119 7/1975 McMurtrie ................ 308/3 A
4,205,233 5/1980 Craig et al. ................ 378/209
4,552,347 11/1985 Wallis ........................ 378/209

Primary Examiner—Robert C. Watson
Attorney, Agent, or Firm—Burns, Doane, Swecker & Mathis

[57] ABSTRACT

A patient's table for X-ray examinations and radiotherapy includes a couch plate which is guided with longitudinal sliding mobility on a column. In order to obtain precise guidance and low sag of the couch plate in all positions, an intermediate support is included which is arranged at the side on a bar beneath the couch plate. A continuous belt revolving in the intermediate support establishes a mechanical and electrical connection between the guide pedestal and the couch plate and always entrains the intermediate support beneath the couch plate and serves as a prolonged base for the absorption of the changing moments between the couch plate and the guide pedestal.

15 Claims, 6 Drawing Figures

PATIENT'S TABLE

FIELD OF INVENTION

The invention relates to a patient's table of the type having a vertically adjustable couch plate that is horizontally movable in two directions and rotatable about a vertical axis.

BACKGROUND OF THE INVENTION

Patient's tables for X-ray examinations and radiotherapy of the above-mentioned type are known, which are rotatable about a vertical axis and can also be slid longitudinally and transversely to the couch surface. These tables are also adjustable vertically.

In these prior tables, the mechanisms for providing sliding mobility of the couch surface of the table were not vertically compact, particularly those which provided longitudinal sliding far beyond a column supporting the couch surface. Accordingly, these prior designs necessitated substantial thickness and/or height in the frames of the tables. Because of their extra thicknesses, these tables could be collapsed vertically only to a limited extent.

Another disadvantage of the known tables is that they provided insufficient stability when the couch surface was extended to its extreme positions, that is to say fully extended relative to the supporting column.

OBJECTS AND SUMMARY OF THE INVENTION

An object of the invention is the achievement of a patient's table in which the overall height of a couch surface with guideways for permitting transverse and longitudinal sliding movement can be reduced; and its stability, as regards the bracing of the moments with the couch plate extended, improved in spite of a reduced overall height.

The use of an intermediate support attached only at one side, permits the arrangement of all the guideways for longitudinal sliding of the table in a space with low overall height.

In a further embodiment of the invention, the intermediate support includes two steel rails each having two grooves, between which a continuous belt is inserted to revolve around two rollers, by which the couch plate can be driven. A long base for the moments generated by the couch plate and the patient is formed by the intermediate support in the extended position.

A reliable grounding of the couch plate can be ensured by an electrically conductive construction of the belt or a copper foil attached to the belt.

In a further embodiment of the invention, the grooves necessary as counterparts to the grooves in the intermediate support are attached to ribs on the guide pedestal and on a prolongation of the couch plate.

A play-free and therefore also vibration-free guide system is formed by cylindrical rollers with axes positioned mutually at 90° alternately.

The couch plate is advantageously driven by a drive motor, the output pinion of which is in mesh with a tooth system on the intermediate support.

By virtue of the lateral arrangement of the intermediate support, the overall height of the couch surface can be minimized. Also a high bar can be provided beneath the couch plate, which has a favorable influence upon sagging.

DESCRIPTION OF THE DRAWINGS

The invention is described more fully with reference to the accompanying drawings, in which.

DETAILED DESCRIPTION OF THE PREFERRED EMBODIMENTS

Figure 1:
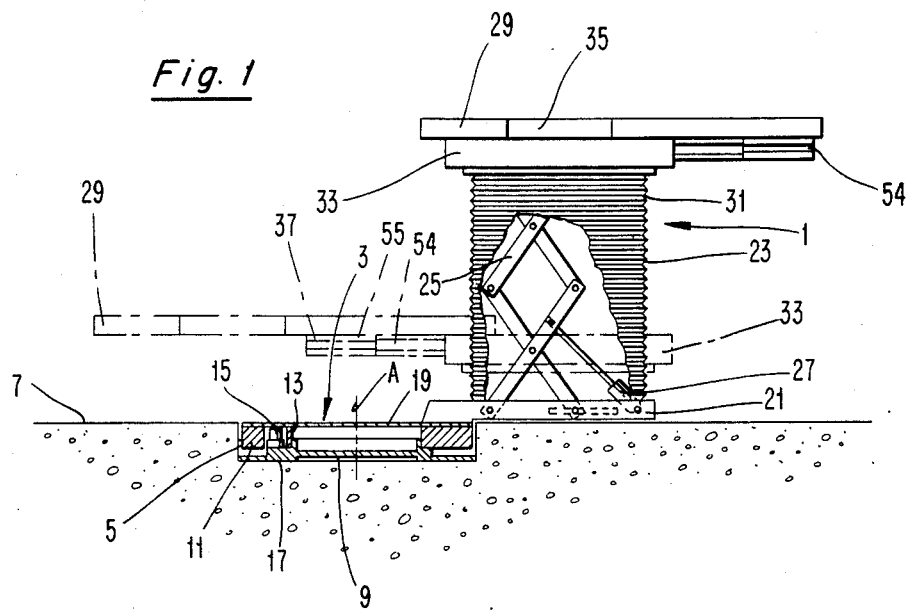
FIG. 1 is a partial cross-sectional view through a patient's table in accordance with a preferred embodiment of the present invention along the line I—I in FIG. 2.

In FIG. 1, a patient's table 1 is mounted rotatably on an axis of rotation A. The rotary bearing 3, which is not a part of the invention and is only described briefly for better understanding, includes a ring gear 9 inserted firmly into a depression 5 in the floor 7, and a ring 11, on the inside of which a ball bearing or roller bearing 13 is placed and braced against the ring gear 9.

A motor gear unit 15, a conventional direct-current motor with a worm gear, for example, is attached to the ring 11 by a drive pinion 17 and is drivably connected to the ring gear 9.

The foot 21 of the column 23 of the table 1 is placed upon the ring 11, which is covered by a disc-shaped plate 19. A scissor-type lift 25, which is located in the column 23, can be transported by a hydraulically driven or electrically driven drive mechanism 27 from a folded position, in which the couch plate 29 of the table 1 occupies the lowered position, into an extended position (Table 1 raised). The column 23 is enclosed by a bellows 31 in order to protect the scissor-type lift 25 and its articulations and guide mechanisms, and also as a protection against accidents.

The couch plate 29 is mounted with longitudinal sliding mobility in a longitudinal guideway of a guide support 33. The guide support 33 is also slidable on the column 23 conjointly with the couch plate 29 tranversely to the longitudinal extent of the couch plate 29. The construction of the transverse guideway is not a part of the invention and is therefore not shown and described in more detail; it may be of similar or identical construction to the longitudinal guideway. A recess 35 may be provided on each side in the couch plate 29 for the attachment of so-called C-arms 36, which when placed outwardly (upwardly) permit an irradiation from underneath, or, when placed inwardly (downwardly), permit a lateral irradiation (FIG. 2).

Figure 2:
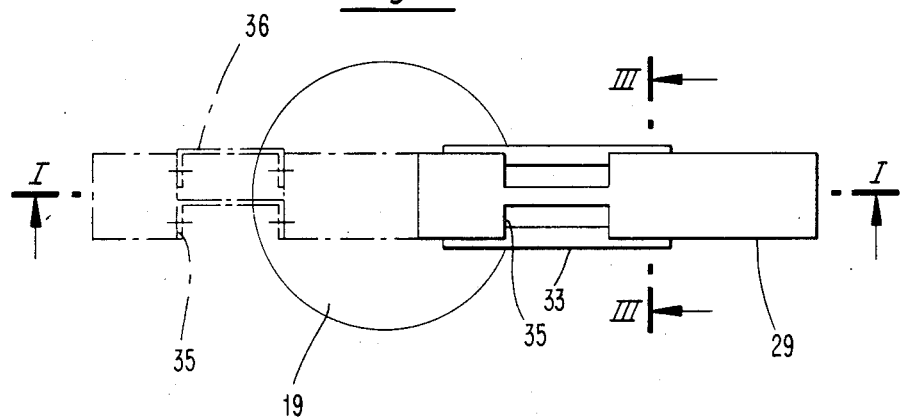
FIG. 2 is a plan view of the patient's table.

The extreme positions of the couch plate 29 are visible in FIGS. 1 and 2; in solid lines on the one hand, the couch plate is extended to the greatest possible height and to the right; in chain-dotted lines the couch plate 29 is extended in the lowest position and fully to the left.

Figure 3:
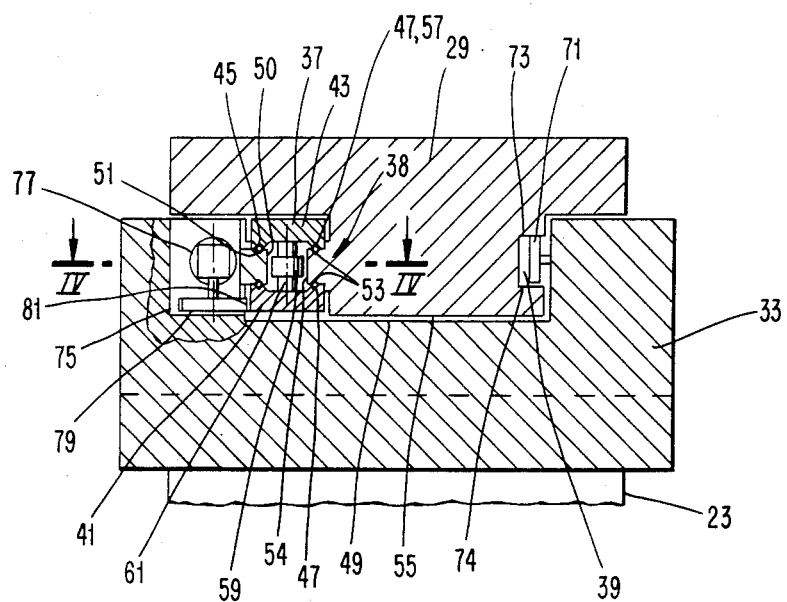
FIG. 3 is a cross-sectional view through the couch surface along the line III—III in FIG. 2.
Figure 4:
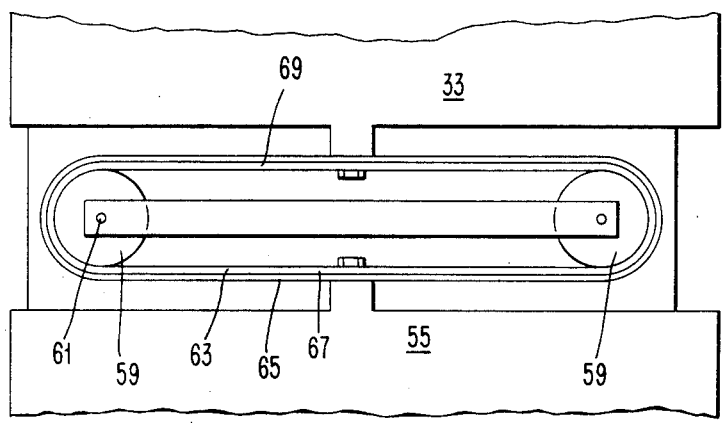
FIG. 4 is a sectional view along the line IV—IV in FIG. 3.

The guideways 37 and 39 for the longitudinal sliding of the couch plate 29 are visible in detail FIG. 3. The guideway 37 includes two spaced steel rails 41, 43 located mutually parallel and firmly mutually connected, forming an intermediate support 38, which has vee-shaped grooves 45, 47 on the mutually facing sides of the rails. As counterparts to the grooves 45 on the rail 43, grooves 51 are made in a recess 49 on the guide pedestal 33, extending along the recess 49 on a rib 50. Analogously, grooves 53, which are set into a bar 55 of the couch plate 29, which bar is provided with a rib 54 and is received in the recess 49, are located opposite the grooves 47. Cylindrical rollers 57, for example, RD type longitudinal guides of Messrs. Schneeberger, Roggwil, Switzerland, are inserted with alternate axial position into the grooves 45, 51 and 47, 53, so that low-friction and precise longitudinal guidance of the couch plate 29 on the guide pedestal 33 is ensured. Grooves of circular arcuate cross-section and balls may also be provided instead of vee-shaped grooves. The intermediate support 38 formed by the rails 41 and 43 includes return rollers 59 attached to the ends of the rails 41 and 43, which are mounted rotatably on vertically fitted axes 61 (see FIG. 4). A continuous belt 63, which is either coated with an electric conductor 65 or is itself of electrically conductive construction, travels over the return rollers 59 in order to establish an electrical connection between the couch plate 29 and the guide pedestal 33. The belt 63 is screwed on one side 67 to the bar 55 of the couch plate 29 and on the other side 69 to the guide pedestal 33, so that a mechanical connection is established between the couch plate 29 and the guide pedistal 33. The height of the intermediate support 38 is preferably equal to or slightly less than the height of the bar 55.

A guideway 39, arranged on the other flank of the bar 55, includes a plurality of rollers 71 arranged in a straight line on the side of the recess 49, which are received in a groove 73 made on the bar 55 of the couch plate 29 and can roll along its flanks 74. A drive motor 77 with a pinion 79 is inserted into a recess 75 on the side of the steel rail 43; this pinion 79 meshes with a tooth system 81 on the rail 41 and can slide the latter along the guide pedestal 33. A type No. 0130 820 072 flat motor with gear from Bosch, in Germany may be used as a drive motor for example.

Figure 5:
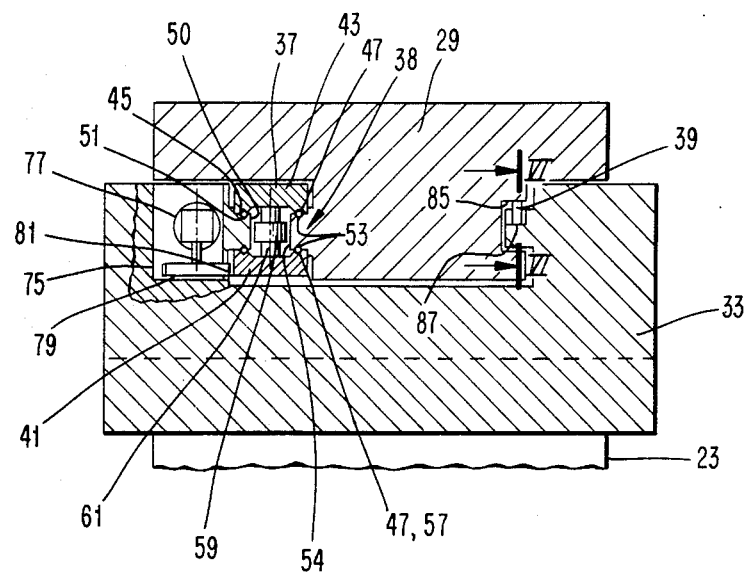
FIG. 5 is a cross-sectional view through the couch surface along the line III—III in FIG. 2.
Figure 6:
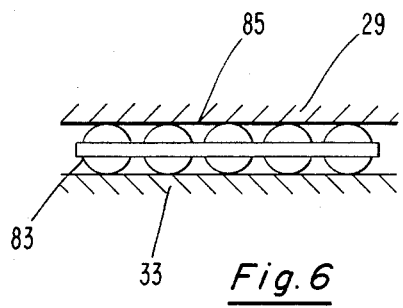
FIG. 6 is a sectional view along the line VI—VI in FIG. 5.

In another embodiment of the invention and as shown in FIGS. 5 and 6 the rollers 71 are replaced by a roller guideway 83, a type JJ ball cage from Messrs. Schneeberger, Roggwil, Switzerland, for example, which is inserted between the rolling surface 85 of the couch plate 29 and the rolling surface 87 on the guide pedestal 33.

Due to the connection of the couch plate 29 to the guide pedestal 33 via the belt 63, the couch plate 29 slides twice as fast and twice as far as the guideway 37 when the latter is driven by the drive motor 77.

In order to slide the couch plate 29 into the extreme left-hand position, that is to say fully extended to the left (FIG. 1), the guideway 37 with the steel rails 41 and 43 is moved to the left by the drive motor 77. Because the motor 77 is connected firmly to the guide pedestal 33 and the guideway 37 is likewise in communication with the guide pedestal 33 through the first side 67 of the continuous belt 63, and the second side 69 is also screwed to the couch plate 29, the latter moves at double speed, and the couch plate 29 always travels twice the distance of the guideway 37. When the couch plate 29 is fully extended, the guideway 37, the length of which corresponds approximately to the length of the guide pedestal 33, is located half inside and half outside the guide pedestal 33. It therefore forms both a precise guideway for the couch plate 29, and also a long base to absorb the moment upon the points of support between the couch plate 29 and the guide pedestal 33 when the couch plate 29 is extended and loaded with a patient.

While this invention has been described in accordance with a preferred embodiment of the invention, it is recognized that variations and changes may be made therein without departing from the invention as set forth in the claims.

I claim:

1. In a patient's table of the type having drive means, longitudinal guideways and a vertically adjustable couch plate, said couch plate slidable horizontally along said longitudinal guideways and rotatable about a vertical axis, said drive means driving the table about the vertical axis and the couch plate horizontally along said longitudinal guideways, the improvement comprising a guide pedestal supporting the couch plate and two mutually independent guideways spaced apart from each other, said guideways respectively provided between the couch plate and said guide pedestal for the sliding of the couch plate in the longitudinal direction, one of said guideways provided with a support member, means for slidably engaging said support member with said couch plate and said guide pedestal, whereby said support member may guide the sliding of the couch plate and means for moving said support member concurrently with said couch plate such that said couch plate moves twice a distance that said support member is moved, whereby stability of said couch plate at its fully extended position may be enhanced.

2. In a patient's table of the type having a vertically adjustable couch plate slidable horizontally in a longitudinal direction by means of longitudinal guideways and rotatable about a vertical axis and with drive means to drive the table about the vertical axis of rotation and the couch plate along the sliding paths in the guideways, the improvement comprising two mutually independent guideways spaced apart from each other are respectively provided between the couch plate and a guide pedestal supporting the couch plate for the sliding of the couch plate in the longitudinal direction, one of said guideways providing an intermediate support, the intermediate support having two steel profiles each having two grooves between which a continuous belt is arranged revolving round two rollers rotatable about two axes attached horizontally to the couch plate, which belt has two sides which are located parallel to the intermediate support, with the belt being connected on the first side to the guide pedestal and on the second side to the couch plate.

3. The patient's table according to claim 2, wherein the belt is constructed as an electric conductor.

4. The patient's table according to claim 3, wherein a copper belt is attached to the belt as an electric conductor.

5. The patient's table according to claim 2, wherein a pair of ribs having two grooves engages respectively between the grooves on the intermediate support, one of said ribs being a part of the guide pedestal and the other rib being a part of a bar on the couch plate.

6. The patient's table according to claim 2, wherein cylindrical rollers are inserted substantially free from play and alternately with axes located mutually at 90° between the grooves.

7. The patient's table according to claim 2, wherein a tooth system, with which a pinion of a drive motor meshes, is attached to one of the steel profiles.

8. The patient's table according to claim 5, wherein the intermediate support is arranged at the side of the bar of the couch plate.

9. The patient's table according to claim 8, wherein the height of the intermediate support is less than or equal to the height of the bar.

10. A patient's table, comprising:
a couch plate;
supporting means for said couch plate;
said supporting means including a guide pedestal mounting means for sliding said couch plate horizontally along a longitudinal axis relative to said guide pedestal;
said mounting means including two mutually independent guideways spaced apart from each other between said couch plate and said guide pedestal; and
a support member in one of said guideways, means for slidably engaging said support member with said couch plate and said guide pedestal whereby said support member may guide the sliding of the couch plate and means for coupling said support member with said couch plate and said guide pedestal so that when said couch plate is moved a first distance said support member is moved a second distance half of said first distance, whereby stability of said couch plate at its fully extended position may be enhanced.

11. A patient's table, comprising:
a couch plate;
supporting means for said couch plate;
said supporting means including a guide pedestal mounting means for sliding said couch plate horizontally along a longitudinal axis relative to said guide pedestal;
said mounting means including two mutually independent guideways spaced apart from each other between said couch plate and said guide pedestal; and
roller means in one of said guideways for supporting said couch plate in both the longitudinal and transverse directions as said couch plate slides longitudinally relative to said guide pedestal;
said roller means including a pair of rollers mounted on said couch plate and rotatable about vertical axes; a continuous belt supported between said rollers and having two sides that are disposed parallel to said longitudinal axis, one of the sides of said belt being connected to said guide pedestal and the other side being connected to said couch plate.

12. The patient's table according to claim 11, wherein the belt is an electric conductor.

13. The patient's table according to claim 12, wherein the belt includes a copper belt.

14. The patient's table according to claim 11, wherein said roller means includes first and second ribs each having grooves that are located between grooves on the intermediate support, the first rib being a part of the guide pedestal and the second rib being a part of a bar on the couch plate.

15. The patient's table according to claim 14, including a pinion and a drive motor for driving said pinion; and wherein one of said ribs has a tooth system thereon, said pinion meshing with said tooth system.

* * * * *